United States Patent [19]
Deeba et al.

[11] 4,434,300
[45] Feb. 28, 1984

[54] METHANOL AMINATION

[75] Inventors: Michel Deeba, Emmaus; William J. Ambs, Swarthmore; Robert N. Cochran, West Chester, all of Pa.

[73] Assignee: Air Products and Chemicals, Inc., Allentown, Pa.

[21] Appl. No.: 417,293

[22] Filed: Sep. 13, 1982

[51] Int. Cl.$^3$ .............................................. C07C 85/06
[52] U.S. Cl. ..................................................... 564/479
[58] Field of Search ......................................... 564/479

[56] References Cited

U.S. PATENT DOCUMENTS

| | | | |
|---|---|---|---|
| 2,092,431 | 9/1937 | Swallen et al. | 564/479 |
| 2,113,241 | 4/1938 | Punnett | 564/479 |
| 3,384,667 | 5/1982 | Hamilton | 260/585 |
| 4,082,805 | 4/1978 | Kaeding | 260/585 |
| 4,191,709 | 3/1980 | Parker et al. | 260/583 |
| 4,205,012 | 5/1980 | Parker et al. | 260/583 |
| 4,213,882 | 7/1980 | Kranich, Jr. | 252/455 |
| 4,217,240 | 8/1980 | Bergna | 564/479 X |
| 4,229,374 | 10/1980 | Slaugh et al. | 260/563 |
| 4,254,061 | 3/1981 | Weigert | 564/479 |

Primary Examiner—Paul F. Shaver
Attorney, Agent, or Firm—Michael Leach; E. Eugene Innis; James C. Simmons

[57] ABSTRACT

A process for improving the methanol conversion rate in the reaction of methanol and ammonia to produce methylamines which comprises effecting the reaction in the presence of a macroporous, highly acidic aluminosilicate catalyst. Macroporous H-chabazite-erionite is the preferred catalyst.

8 Claims, No Drawings

METHANOL AMINATION

TECHNICAL FIELD

This invention relates to the preparation of methylamines by a catalytic reaction between methanol and ammonia.

BACKGROUND OF THE INVENTION

The catalyzed reaction of methanol and ammonia to produce the mono-, di-, and trimethylamines is well known in the art. Presently, the methylamines are produced commercially by a continuous process for methanol and ammonia using an amorphous silica-alumina catalyst. This continuous process yields an equilibrium controlled distribution of the methylamines.

U.S. Pat. No. 3,384,667 discloses a method for producing monosubstituted and disubstituted amines in preference to trisubstituted amines by reacting ammonia with an alcohol in the presence of a crystalline metal aluminosilicate catalyst having pores of a diameter that passed the monosubstituted and disubstituted amine products, but are too small to pass the trisubstituted amine product.

U.S. Pat. No. 4,082,805 discloses a process for the production of aliphatic amines by reaction of a $C_1$-$C_5$ alcohol or ether with ammonia in the presence of a catalyst comprising a crystalline aluminosilicate having the structure of ZSM-5, ZSM-11 or ZSM-21, at 300° to 500° C. and at 1 atm to 1,000 psig pressure, the feed rate of alcohol or ether and ammonia being within the ratio of 1:1 to 5:1 g/hr.

U.S. Pat. No. 4,191,709 discloses a process for the manufacture of amines by reacting an alcohol with ammonia in the presence of the hydrogen form of zeolite FU-1 or zeolite FU-1 in which some or all of the protons have been replaced by bivalent or trivalent cations. The related U.S. Pat. No. 4,205,012 is similar except that the catalyst comprises zeolite FU-1 in which some or all of the protons have been replaced by mono-valent cations, for example, sodium.

U.S. Pat. No. 4,229,374 discloses a process for producing tertiary amines by reacting alcohols with ammonia, primary amines or secondary amines in the presence of a specific catalyst. The catalyst comprises a mixture of copper, tin and an alkali metal supported on a suitable carrier, such as artificial and natural zeolites.

U.S. Pat. No. 4,254,061 discloses a process for producing monomethylamine by reacting methanol and ammonia, in such amounts so as to provide a C/N ratio, from the methanol and ammonia reactants, of 0.5-1.5, over a catalyst which is (a) mordenite wherein the primary cation is Li, Na, HNa having at least 2% Na by weight, K, Ca, Sr, Ba, Ce, Zn or Cr; (b) ferrierite wherein the primary metal cation is Li, Na, K, Ca, Sr, Ba, Ce or Fe; (c) erionite ore; (d) calcium erionite; or (e) clinoptilolite ore.

The methanol amination reaction is exothermic. Thus, in an adiabatic plug flow reactor for the production of methylamines, the temperature rises by about 150°-400° F. (83°-222° C.) depending on the ammonia:methanol feed ratio. The maximum allowable reactor temperature for methylamine is about 800° F. (427° C.), above which thermal reactions yielding coke and cracked by-products make the process inoperative.

The present silica-alumina catalysts require feed temperatures above 600° F. (316° C.) to obtain commercial methylamines production requirements. With a starting temperature of 600° F. (316° C.), the molar feed ratio of ammonia:methanol must be higher than 2 for the maximum temperature in an adiabatic reactor to be less than 800° F. (427° C.). Therefore, greater than two-fold excess ammonia over the stoichiometric requirement must be used to avoid coking and cracking. Use of such excess ammonia means large ammonia separation stills to recycle the ammonia.

Thus, improving the methanol conversion rate would offer advantages such as lower inlet temperatures permitting lower ammonia:methanol feed ratios and less excess ammonia to handle.

SUMMARY OF THE INVENTION

In accordance with this invention, there is provided a method for improving the methanol conversion rates in the production of methylamines by the reaction of methanol with ammonia in the presence of a catalyst. The invention comprises reacting methanol and ammonia under conversion conditions in the presence of a macroporous, highly acidic aluminosilicate catalyst having a silicon to aluminum (Si:Al) ratio of greater than about 2.0.

Macroporous hydrogen exchanged chabazite-erionite, which is the preferred aluminosilicate catalyst for practicing the invention, surprisingly showed methanol conversion rates which were greatly improved compared to amorphous silica-alumina while its ethanol conversion rates showed a smaller improvement over silica-alumina at lower temperatures (up to about 700° F.) and were less than the silica-alumina conversion rates at higher temperatures. The selectivity to the formation of methylamines was high in contrast to the ethanol conversion situation in which the yield of ethylene was relatively high.

Since the macroporous, highly acidic aluminosilicate catalysts are more active, i.e., show greater enhanced activity at lower temperatures, advantageously lower reactor inlet temperatures can be used while achieving the same methanol conversion rates previously achieved with prior art catalysts.

Thus, the process of this invention permits the use of lower ammonia:methanol ratios in the feed stream without exceeding 800° F. (427° C.) in the reactor, i.e., use less excess ammonia in the reaction and remain below 800° F.

In addition, where a catalyst of the invention, for example, exhibits an x-fold increase in methanol conversion rate over a prior art catalyst, the substitution of such catalyst in the methylamines production scheme for the prior art catalyst means the scheme could advantageously be operated at the same temperature with a reactor 1/x the size while maintaining the same methylamines output, or the production capacity could be increased x-fold using the same size reactor; both represent considerable capital savings.

Several other advantages associated with the inventive process are the following:

Energy savings on preheating of the feed streams are realized because of a lower starting feed temperature.

Since lower ammonia:methanol ratios can be used at lower inlet temperatures, less excess ammonia needs to be separated from the reaction products by distillation. The ammonia distillation column can be much smaller and thus consume less energy.

In addition, thermal reactions leading to by-products and catalyst coking should be less at lower temperatures.

DETAILED DESCRIPTION OF THE INVENTION

The invention relates to an improved catalytic process for preparing methylamines from methanol and ammonia. More particularly, the invention provides surprisingly improved methanol conversion rates by contacting methanol with ammonia in the presence of a macroporous, highly acidic aluminosilicate catalyst having a silicon to aluminum (Si:Al) ratio of about 2.0 or greater, preferably 2.5 or greater.

Alcohol amination requires acidic materials to perform the reaction. The higher the acidity of the material, in terms of the number and strength of acidic sites in a zeolitic catalyst, the higher should be the rate for alcohol amination.

The complete description of surface acidic properties of a solid with high surface area must involve the determination of the acid strength $H_o$, the density, the nature and the position of acidic sites. However, the surface heterogeneity complicates the measuring of acidic distribution in its correlation with catalytic activity. Thus, a comparison of the acidity and activity properties of different materials is not straight forward due to the absence of a quantitative model for relating the physicochemical properties of different surfaces.

Therefore, an ammonia adsorptivity procedure which gives the distribution of acidic sites as a function of temperature was chosen for evaluating the acidity of a catalyst surface. It has been discovered that a material which shows high ammonia adsorptivity and therefore high acidity does not, by itself, mean it is a good catalyst for methanol amination. On the other hand, a material which shows very low acidity by the ammonia adsorptivity procedure would be expected to give low methanol conversion rates.

The ammonia adsorptivity procedure which was used for measuring the acidity of solid surfaces is the following:

Acidity distribution was measured using a thermal gravimetric analysis technique with ammonia as the adsorbate. The acidity measurement was performed by activating about 20 to 40 mg of a catalyst at temperatures up to 400° C. in helium after which the catalyst was cooled to 25° C. The catalyst was then exposed to ammonia. The uptake of ammonia by the catalyst was very fast and the catalyst surface was saturated within 5 minutes.

Helium was then used to desorb the physically adsorbed ammonia at 25° C. followed by desorption by heating the catalyst to 100°, 200°, 300° and 400° C., respectively. The temperature was raised to the next level after there was no change in the rate of desorption as indicated by decreasing weight of the catalyst. The amount of irreversibly adsorbed ammonia at each temperature was taken as a count of acidic sites. The amount of irreversibly adsorbed ammonia at 25° and 100° C. was considered as a measurement of total acidity (both weakly and strongly acidic sites) and that amount of ammonia irreversibly adsorbed at 200° and 300° C. as a measurement of strongly acidic sites. The strongly acidic sites are believed to be the important locales for the amination reaction.

TABLE I

| Catalyst | Irreversibly Adsorbed Ammonia (mmole/g catalyst) Temperature (°C.) | | | | |
|---|---|---|---|---|---|
| | 25 | 100 | 200 | 300 | 400* |
| H—erionite | 4.0 | 1.9 | 1.5 | 1.0 | — |
| H—clinoptilolite | 3.6 | 2.1 | 1.2 | 0.8 | — |
| H—mordenite | 3.3 | 2.2 | 1.4 | 0.56 | — |
| REY zeolite | 3.3 | 1.8 | 0.9 | 0.4 | — |
| H—Y zeolite | 3.6 | 2.3 | 1.2 | 0.5 | — |
| H—chabazite-erionite (macroporous) | 3.6 | 1.8 | 1.08 | 0.45 | — |
| silica-alumina (amorphous) | 0.3 | 0.09 | trace | — | — |

*At 400° C. ammonia desorption was complete.

Table I shows the acidity values of various zeolite catalysts in terms of millimoles of irreversibly adsorbed ammonia per gram of catalyst of the designated temperatures. As one characteristic of the macroporous crystalline aluminosilicate catalyst suitable for practicing the process of this invention, the catalyst should be able to irreversibly adsorb at least 0.5 mmole ammonia, preferably 0.8 mmole ammonia, per gram of catalyst at 200° C. Ideally at least 1.0 mmole ammonia/g catalyst should be irreversibly adsorbed at 200° C. as exemplified by macroporous H-chabazite-erionite which contained at least about 20% chabazite.

The high acidity value of a catalyst, as determined by the amount of ammonia irreversibly adsorbed at 200° C., is not the only requirement for catalytic activity of methanol amination. The catalyst must also possess a minimum degree of macroporosity. Macroporosity is that property of a heterogeneous catalyst whereby the catalyst possesses a sufficient volume of large pores (macropores) so that the desired reaction is not hindered by diffusion limitations. With respect to the methanol amination process of the invention, suitable macroporous aluminosilicates should have sufficient macropores larger than 30 Angstroms in diameter to give a mercury intrusion volume of at least 0.3 cc mercury/g catalyst at about 60,000 psia (4080 atm). Preferably, the catalyst of the invention should have sufficient macropores larger than 50 Angstroms to give a mercury intrusion volume of at least 0.3 cc mercury/g catalyst at about 30,000 psia (2040 atm).

A mercury porosimeter is used to determine the pore size distribution of catalysts. Mercury is a non-wetting liquid having a contact angle ($\theta$) of about 130°. Assuming that all pores of the catalyst are equally accessible, only those pores will be filled with mercury for which $$r = \frac{4 \mu \cos \theta}{P_c}$$

where
r = pore diameter
$\mu$ = surface tension; for mercury = 0.474 Nm$^{-1}$
$\theta$ = contact angle; for mercury = 130°
$P_c$ = pressure difference Each increment of applied pressure causes the next group of pores having a smaller diameter to be filled with a concomitant increase in the total volume of mercury penetrating into the solid. Thus, a method is provided for obtaining quantitative information on macropore distribution.

For example, using a contact angle of 130° and a surface tension of about 0.477 N/m, the minimum pore diameter which will just permit mercury penetration at a pressure of about 14,000 psia (952 atm) is 122 Angstroms.

The determination of the pore diameter distribution requires a measurement of the volume of mercury forced into the pore space of a material as a function of the applied pressure. The resulting data can be used to calculate that part of the specific surface area of the porous material which is accessible to mercury.

The following is a general preparative procedure for making a macroporous hydrogen exchanged aluminosilicate catalyst (H-catalyst). The H-exchanged zeolites can be prepared by mixing extrusions of the sodium or potassium form of the zeolite with an aqueous ammonium salt, such as ammonium chloride or ammonium nitrate, in appropriate amounts under controlled pH of about 3-4. The mixture is then refluxed for several hours (8-12 hr). The supernatant is decanted and the aqueous ammonium salt treatment is repeated two more times. Finally, the solids are removed, washed with water under reflux conditions and air-dried, preferably at an elevated temperature of about 120° C. The dried, ammonium exchanged material is thoroughly mixed with a pore forming agent such as corn starch and pelletized. The pellets are heat treated at about 1,000° F. (538° C.) for several hours in flowing air saturated with 10% ammonium hydroxide solution followed by two hours in dry air.

The teaching in U.S. Pat. No. 4,213,882 is applicable to the preparation of macroporous aluminiosilicate catalysts for the methanol amination reaction and is incorporated by reference.

Macroporous, highly acidic aluminosilicate catalysts which can be prepared following the general procedure and are suitable for the inventive process include, for example, macroporous H-erionite, macroporous H-clinoptilolite, macroporous H-mordenite, macroporous H-Y zeolite and macroporous H-chabazite-erionite which is the preferred catalyst for methanol amination.

The sodium or potassium aluminosilicates may be ion exchanged with other metal ions, in particular, polyvalent metal ions, as is well known in the art, and then mixed with a pore forming agent such as corn starch, pelletized and heat treated to yield a macroporous metal ion exchanged aluminosilicate. An example of a suitable metal ion exchanged aluminosilicate catalyst for the amination of methanol is macroporous rare earth Y zeolite (REY zeolite).

Process variables of this invention include the ammonia:methanol ratio, temperature, pressure and contact time or flow rate expressed in terms of gas hourly space velocity (GHSV). Generally the mole ratio of ammonia to methanol may range from about 1:1 to 5:1, and preferably ranges from about 1.5:1 to 2.5:1. If monomethylamine is the desired product, it is advantageous to carry out the process with the proportion of methanol to ammonia in a stoichiometric excess, e.g., up to about 3:1 or more.

In the preparation of the methylamines according to the process of this invention, the reaction is maintained at a temperature from about 450° F. (232° C.) to about 800° F. (427° C.), and preferably from about 550° to 750° F. (288° to 399° C.). If the temperature is too low, the conversion of methanol and ammonia to methylamines will be low requiring excessive contact times or, equivalently, low flow rates. If the temperature is too high, hydrocarbon by-product formation and catalyst coking becomes a significant problem.

The pressure utilized for carrying out the reaction is a pressure between about 1 to 50 atm with a pressure range of about 10 to 30 atm being preferred.

Generally, flow rates (GHSV) of about 1,000 to 30,000 ml of methanol/cc of catalyst/hour, preferably 5,000 to 15,000 ml of methanol/cc of catalyst/hour, may be used.

Contemplated as the operative, or functional, equivalent of methanol for use in the process of this invention is its ether derivative, dimethyl ether.

The invention resides in the unexpectedly superior methanol conversion rates associated with the macroporous, highly acidic aluminosilicate catalysts, using silica-alumina as a basis of comparison. In contrast, the ethanol conversion rates for these catalysts show a lesser degree of improvement over silica-alumina at temperatures of 650° F. or less and, surprisingly, are inferior at 750° F. The term methanol conversion rate means the rate at which methanol is converted to methylamines per gram of catalyst as expressed by the equation:

$$\text{Rate} = \frac{\text{g-mole } (MMA + 2DMA + 3TMA)}{\text{g-catalyst-second}}$$

where MMA=monomethylamine, DMA=dimethylamine and TMA=trimethylamine.

The following examples illustrate the nature of the process described herein and are not intended to limit the scope of the invention.

EXAMPLE 1

A series of Runs 1-4 were made to produce methylamines. Methanol and ammonia in such amounts so as to provide an ammonia:methanol molar ratio of about 2:1 were passed over about 5.34 grams of catalyst in a Berty recycle reactor which is a fixed bed reactor with a large (greater than 20) internal recycle ratio. Under these conditions the Berty reactor is gradientless and behaves like a continually stirred tank reactor (CSTR). Rates of reaction can be calculated directly as moles converted per gram of catalyst per second of residence time.

The reaction was performed at a total pressure of 18 atm at a gas hourly space velocity of 9,300 and at a variety of temperatures from 550° to 750° F. (288° to 399° C.). The reactor feeds and effluent were analyzed by an on-line gas chromatograph. The streams were maintained gaseous from the reactor to the chromatograph sampling valve. The catalysts tested were those listed in Table II, including amorphous silica-alumina, macroporous H-chabazite-erionite, and H-erionite.

The amorphous silica-alumina was a Ketjen LA-30 catalyst.

The macroporous H-chabazite-erionite catalyst was prepared from Anaconda 5050F (chabazite-erionite, at least about 20% chabazite) powder which was exchanged three times using 10% aqueous ammonium nitrate for each exchange and reslurrying after each filtration. The material was washed three times on the filter using deionized water each time and then dried at 250° F. (121° C.) without air circulation. The dried, ammonium exchanged material was mixed thoroughly with corn starch and $\frac{1}{8}''$ diameter$\times\frac{1}{8}''$ length (32 mm$\times$32 mm) pellets were prepared. The pellets were heat treated at 1,000° F. (538° C.) for two hours in flowing air saturated with 10% ammonium hydroxide solution followed by two hours in dry air.

Table II sets forth the methanol conversion rates in terms of gram-mole methanol/grams catalyst-second for the catalyst tested at the designated temperatures.

temperatures of about 600° F. (316° C.) or below, macroporous H-chabazite-erionite afforded extraordinarily high methanol conversion rates compared to amorphous silica-alumina. At 700° F. (371° C.) and 750° F. (399° C.), macroporous H-chabazite-erionite showed

TABLE II

| | METHANOL CONVERSION RATES (g mol CH$_3$OH/g cat sec) | | | | |
|---|---|---|---|---|---|
| | TEMPERATURE | | | | |
| CATALYST | 550° F. (288° C.) | 600° F. (316° C.) | 650° F. (343° C.) | 700° F. (371° C.) | 750° F. (399° C.) |
| 1 Silica-alumina | $5.0 \times 10^{-7}$ | $1.5 \times 10^{-6}$ | $5.2 \times 10^{-6}$ | $1.5 \times 10^{-5}$ | $3.7 \times 10^{-5}$ |
| 2 5A zeolite | $24.7 \times 10^{-7}$ | $5.4 \times 10^{-6}$ | $12.3 \times 10^{-6}$ | $2.0 \times 10^{-5}$ | — |
| 3 H—chabazite-erionite (macroporus) | $149 \times 10^{-7}$ | $26.5 \times 10^{-6}$ | $36.2 \times 10^{-6}$ | $5.4 \times 10^{-5}$ | $7.7 \times 10^{-5}$ |
| 4 H—erionite | $75 \times 10^{-7}$ | $14.3 \times 10^{-6}$ | $23.7 \times 10^{-6}$ | $3.4 \times 10^{-5}$ | $4.6 \times 10^{-5}$ |

The 5 A zeolite catalyst suffered from poor hydrothermal stability at the higher temperatures which, it is believed, explains its approach to the behaviour of amorphous silica-alumina at about 700° F. (371° C.) and the lack of data at 750° F. (399° C.). This instability is related to its low Si:Al ratio of about 1. A Si:Al ratio of about 2.0 or greater is required in the zeolite for it to have the necessary hydrothermal stability at the conversion conditions for the amination of methanol.

The following listing of the Si:Al ratios for several zeolites was obtained from D. W. Breck, *Zeolite Molecular Sieves*, John Wiley & Sons, 1974:

methanol conversion rates which were at least 50% higher than H-erionite and at least 100% higher than amorphous silica-alumina.

TABLE III

| | COMPARISON OF METHANOL CONVERSION RATES (ALUMINOSILICATE CATALYST/SILICA-ALUMINA CATALYST) | | | | |
|---|---|---|---|---|---|
| | TEMPERATURE | | | | |
| CATALYST | 550° F. (288° C.) | 600° F. (316° C.) | 650° F. (343° C.) | 700° F. (371° C.) | 750° F. (399° C.) |
| 1 Silica-alumina | 1 | 1 | 1 | 1 | 1 |
| 2 5A zeolite | 4.9 | 3.6 | 2.4 | 1.3 | — |
| 3 H—chabazite-erionite (macroporus) | 30 | 18 | 7.0 | 3.6 | 2.1 |
| 4 H—erionite | 15 | 9.5 | 4.6 | 2.3 | 1.2 |

TABLE IV

| | COMPARISON OF METHYLAMINES PRODUCT SPLIT (mole % MMA, mole % DMA, mole % TMA) | | | | |
|---|---|---|---|---|---|
| | TEMPERATURE | | | | |
| CATALYST | 550° F. (288° C.) | 600° F. (316° C.) | 650° F. (343° C.) | 700° F. (371° C.) | 750° F. (399° C.) |
| 1 Silica-alumina | (59, 25, 15) | (35, 11, 43) | (31, 27, 42) | (33, 27, 40) | (34, 28, 37) |
| 2 5A zeolite | (82, 18, 0) | (70, 30, 0) | (56, 31, 13) | (38, 31, 31) | — |
| 3 H—chabazite-erionite (macroporus) | (69, 31, 0) | (54, 46, 0) | (48, 42, 10) | (47, 43, 11) | (46, 41, 13) |
| 4 H—erionite | (87, 13, 0) | (81, 19, 0) | (74, 26, 0) | (67, 33, 0) | (60, 34, 6) |

| Zeolite | Si:Al |
|---|---|
| Erionite | 3–3.5 |
| Chabazite | 1.6–3.0 |
| Mordenite | 4.5–5.0 |
| A | 1.0 |
| X | 1.2 |
| Y | 2.5 |
| ZSM-5 | 6 |

The conversion rates of the various aluminosilicate catalysts are compared to the prior art amorphous silica-alumina catalyst in Table III. As can be seen from the data in Table III, the macroporous, highly acidic aluminosilicate catalyst of the inventive process, namely macroporous H-chabazite-erionite, exhibited superior methanol conversion rates in the temperature range from about 550° F. (288° C.) to about 750° F. (399° C.). At Table IV shows the methylamines product split in the reactor effluent stream. The mole percentages of monomethylamine (MMA), dimethylamine (DMA) and trimethylamine (TMA) were calculated based on the calibrated areas under the chromatogram curves for each amine.

Mono- and dimethylamine were formed over macroporous H-chabazite-erionite and H-erionite with small amounts of trimethylamine at high temperatures.

The acidity of H-chabazite-erionite is less than that of H-erionite at 200° C. (Table I), but the methanol conversion rate for H-chabazite-erionite is greater due to its macroporosity. Thus, high acidity and macroporosity combined in the H-chabazite-erionite catalyst to yield higher methanol conversion rates. All the zeolites tested showed higher methanol conversion rates than silica-alumina due to their higher acidity.

Since the combination of H-chabazite and H-erionite as H-chabazite-erionite is less acidic than H-erionite alone, it seems apparent that H-chabazite would be less acidic than either H-erionite or H-chabazite-erionite and would demonstrate a correspondingly lower methanol amination reaction rate.

The following Examples show that the catalysts which were more active than silica-alumina for methanol amination were surprisingly not nearly as active for ethanol amination and yielded large amounts of ethylene at the higher temperatures.

EXAMPLE 2

The procedure for Runs 1–4 was followed replacing methanol with ethanol in Runs 5–7. Table V shows the ethanol conversion rates of the various catalysts. Table VI compares these rates to amorphous silica-alumina and Table VII shows the amount of ethylene produced.

TABLE V

Ethanol Conversion Rates
(g mole $C_2H_5OH$/g cat sec)

| CATALYST | TEMPERATURE | | |
|---|---|---|---|
| | 550°F. (288° C.) | 650° F. (343° C.) | 750° F. (399° C.) |
| 5 silicate alumina | $0.36 \times 10^{-7}$ | $1.4 \times 10^{-6}$ | $4.6 \times 10^{-6}$ |
| 6 H—chabazite-erionite (macroporous) | $4.4 \times 10^{-7}$ | $3.6 \times 10^{-6}$ | $3.5 \times 10^{-6}$ |
| 7 H—erionite | — | $1.1 \times 10^{-6}$ | $2.6 \times 10^{-6}$ |

TABLE VI

Comparison of Ethanol Conversion Rates
(Aluminosilicate Catalyst/Silica-Alumina Catalyst)

| CATALYST | TEMPERATURE | | |
|---|---|---|---|
| | 550°F. (288° C.) | 650° F. (343° C.) | 750° F. (399° C.) |
| 5 Silica-alumina | 1 | 1 | 1 |
| 6 H—chabazite-erionite (macroporous) | 12.4 | 2.6 | 0.8 |
| 7 H—erionite | — | 0.8 | 0.6 |

TABLE VII

Ethylene Yield (%)

| CATALYST | TEMPERATURE | | |
|---|---|---|---|
| | 550°F. (288° C.) | 650° F. (343° C.) | 750° F. (399° C.) |
| 5 Silica-alumina | 0 | 0 | 4.7 |
| 6 H—chabazite-erionite (macroporous) | 0 | 7 | 22 |
| 7 H—erionite | — | 10 | 42 |

From Tables V, VI and VII it can be seen that the two acidic aluminosilicate catalysts were not as active for ethanol amination as would have been expected based on their acidity and their methanol amination activity.

At 550° F. (288° C.) and 650° F. (343° C.) the rate of ethanol conversion for the macroporous H-chabazite-erionite catalyst was higher than for silica-alumina. At 750° F. (399° C.), however, the rate of conversion over silica-alumina was higher than for either of the aluminosilicates in spite of the much lower acidity of silica-alumina.

A study of the methanol and ethanol conversion rates of the various catalysts compared to amorphous silica-alumina (Tables III and VI) shows that macroporous H-chabazite-erionite rates are 30 and 12.4 at 550° F.; 7 and 2.6 at 650° F.; and 2.1 and only 0.8 at 750° F., respectively. Thus the catalyst of this invention was surprisingly more effective for methanol conversion than for higher alcohol conversion. Because of its macroporosity, the macroporous H-chabazite-erionite would not have been expected to show such a difference in alcohol amination rates.

Silica-alumina was the most effective catalyst for ethanol conversion.

The reaction of ethanol, and probably higher alcohols, with ammonia was shown to be quite different from methanol amination. High selectivity to amines and almost no by-products were observed with methanol over the crystalline aluminosilicates. Ethanol conversion over the same aluminosilicates indicated higher activity which was misleading since careful analysis of the products showed that selectivity to amines was much lower than for the methanol reaction. A high yield of ethylene was observed for the ethanol reaction which may be related to the very high acidity of the catalysts.

EXAMPLE 3

Macroporous H-chabazite-erionite and H-erionite were tested on a mercury porosimeter. Table VIII presents a comparison of the macroporous properties of the two catalyst materials.

TABLE VIII

| Pressure (psia) | Pore Diameter (A) | H—erionite | | H—chabazite-erionite | |
|---|---|---|---|---|---|
| | | Intrusion Volume (cc/g) | Pore Surface ($m^2$/g) | Intrusion Volume (cc/g) | Pore Surface ($m^2$/g) |
| 10 | 168,000 | 0.024 | 0.005 | 0.001 | 0.000 |
| 20 | 85,400 | 0.053 | 0.015 | 0.006 | 0.002 |
| 40 | 43,600 | 0.074 | 0.028 | 0.008 | 0.003 |
| 100 | 17,100 | 0.13 | 0.10 | 0.014 | 0.011 |
| 200 | 8,590 | 0.15 | 0.19 | 0.024 | 0.043 |
| 500 | 3,370 | 0.18 | 0.40 | 0.073 | 0.44 |
| 1,000 | 1,710 | 0.20 | 0.65 | 0.12 | 1.24 |
| 2,000 | 853 | 0.21 | 1.02 | 0.16 | 2.76 |
| 5,000 | 340 | 0.22 | 1.92 | 0.24 | 7.93 |
| 8,000 | 214 | 0.22 | 2.31 | 0.27 | 13.17 |
| 10,000 | 171 | 0.22 | 2.58 | 0.29 | 17.18 |
| 14,000 | 122 | 0.23 | 2.85 | 0.32 | 25.72 |
| 20,000 | 85 | 0.23 | 3.38 | 0.34 | 34.83 |
| 30,000 | 57 | 0.23 | 3.67 | 0.36 | 45.29 |
| 35,000 | 48 | 0.23 | 4.28 | 0.37 | 48.71 |
| 40,000 | 42 | 0.23 | 4.62 | 0.37 | 51.08 |
| 50,000 | 34 | 0.23 | 5.43 | 0.37 | 54.90 |
| 60,000 | 29 | 0.23 | 7.91 | 0.38 | 60.13 |

Pores with a diameter of at least 29 Angstroms will be filled with mercury when 60,000 psia pressure is applied, thus providing a measure of total pore volume. From Table VIII it can be seen that H-erionite had a total pore volume of about 0.23 cc/g and a total pore surface area of 7.91 $m^2$/g for pores with a minimum diameter of 29 Angstroms. For macroporous H-chabazite-erionite the respective values were 0.38 cc/g and 60.13 $m^2$/g. Thus, macroporous H-chabazite-erionite possessed a macroporosity which was 65% greater than crystalline H-erionite and resulted in the improved catalyst activity.

The sorption cavities of chabazite and erionite constitute, a three dimensional network of pores which is known as the micropores and is a property of the zeolite crystal.

In erionite each cavity has a 15.1 Angstrom length and a 6.6 Angstrom free cross-sectional diameter with a 3.6×5.2 Angstrom diameter cavity opening. Chabazite cavities have an 11 Angstrom length and a 6.5 Angstrom diameter. The diameter of the cavity entrance is 4.4×3.1 Angstroms. Erionite cavities are larger than that of chabazite and for that reason should be more active than the chabazite-erionite mixture for methanol amination. Therefore, since macroporous H-chabazite-erionite has been shown more active than crystalline H-erionite, the reasonable conclusion is that macroporous H-chabazite-erionite is superior to crystalline H-chabazite-erionite to at least the same degree.

The difference in catalytic activity is believed to be related to the high macroporosity of the H-chabazite-erionite catalyst obtained by the procedures described previously. The macroporous volume (pores greater than about 30 Angstroms) was 65% greater. Thus the diffusivity of the reactants and products into and out of the catalyst increased allowing more molecules to reach the active sites inside the cavities and, at the same time, allowing easy exit of the products. So, enhancing the macroporosity enhanced the diffusivity and, in turn, the catalytic activity.

STATEMENT OF INDUSTRIAL APPLICATION

The inventive process provides an improved rate of conversion for methanol in its reaction with ammonia to produce the commercially valuable methyl amines which are employed in tanning and in organic synthesis to manufacture compounds such as surface active agents, fungicides and insecticides for agriculture.

We claim:

1. In a process for producing methylamines by reacting of methanol with ammonia in the presence of a catalyst, the method for improving methanol conversion rates which comprises reacting the methanol and ammonia under conversion conditions in the presence of a crystalline aluminosilicate catalyst which irreversibly adsorbs at least 0.5 millimoles of ammonia per gram of catalyst at about 200° C., has a silicon to aluminum ratio of at least about 2.0, and has a mercury intrusion volume of at least 0.3 cc mercury per gram of catalyst at 60,000 psia.

2. The invention of claim 1 wherein the methanol and ammonia are reacted at a temperature from about 450° to 800° F. and a pressure from 1 to 50 atm.

3. The invention of claim 2 wherein the crystalline aluminosilicate catalyst irreversibly adsorbs at least 0.8 millimoles ammonia per gram of catalyst at about 200° C.

4. The invention of claims 1 or 3 wherein the crystalline aluminosilicate catalyst has a mercury intrusion volume of at least 0.3 cc mercury per gram of catalyst at 30,000 psia.

5. The invention of claims 1 or 2 wherein the catalyst is macroporous H-chabazite-erionite.

6. In a process for producing methylamines by reacting of methanol with ammonia in the presence of a catalyst, the method which comprises reacting methanol and ammonia in the presence of a crystalline aluminosilicate which irreversibly adsorbs at least 0.8 millimoles of ammonia per gram of catalyst at about 200° C., has a silicon to aluminum ratio of at least about 2.0, and has a mercury intrusion volume of at least 0.3 cc mercury per gram of catalyst at 30,000 psia at a temperature from about 550° to 750° F., a pressure from 1 to 50 atm, a gas hourly space velocity of 1,000 to 30,000 ml methanol/cc catalyst/hour and an ammonia:methanol feed ratio of about 1:1 to 5:1.

7. The invention of claim 6 wherein the catalyst is macroporous H-chabazite-erionite containing at least about 20% chabazite.

8. The invention of claim 1 wherein a methylamine is recovered.

* * * * *